(12) United States Patent
Bourquin et al.

(10) Patent No.: US 11,964,081 B2
(45) Date of Patent: Apr. 23, 2024

(54) OXYTOCIN RELEASE STIMULATION

(71) Applicant: KONINKLIJKE PHILIPS N.V., Eindhoven (NL)

(72) Inventors: Yannyk Parulian Julian Bourquin, Eindhoven (NL); Natallia Eduardauna Uzunbajakava, Eindhoven (NL); Lili-Marjan Boelens-Brockhuis, Geldrop (NL); Lucja Elzbieta Bartula, Oirschot (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 859 days.

(21) Appl. No.: 16/966,962

(22) PCT Filed: Jan. 30, 2019

(86) PCT No.: PCT/EP2019/052287
§ 371 (c)(1),
(2) Date: Aug. 3, 2020

(87) PCT Pub. No.: WO2019/149774
PCT Pub. Date: Aug. 8, 2019

(65) Prior Publication Data
US 2021/0046226 A1 Feb. 18, 2021

(30) Foreign Application Priority Data
Feb. 5, 2018 (EP) .................................... 18155117

(51) Int. Cl.
*A61M 1/06* (2006.01)
*A61B 18/00* (2006.01)
*A61N 5/06* (2006.01)
(52) U.S. Cl.
CPC ............ *A61M 1/062* (2014.02); *A61M 1/066* (2014.02); *A61M 1/0697* (2021.05);
(Continued)

(58) Field of Classification Search
CPC .... A61M 1/0697; A61M 1/062; A61M 1/066; A61M 2205/052; A61N 5/0613;
(Continued)

(56) References Cited

U.S. PATENT DOCUMENTS

2017/0112983 A1 4/2017 Thorne
2019/0168020 A1* 6/2019 Chao ..................... A61M 21/02

FOREIGN PATENT DOCUMENTS

CN 106913959 A * 7/2017 ........... A61N 5/0625
EP 2172236 4/2010
(Continued)

OTHER PUBLICATIONS

Nussbaum EL, Lilge L, Mazzulli T. Effects of 630-, 660-, 810-, and 905-nm laser irradiation delivering radiant exposure of 1-50 J/cm2 on three species of bacteria in vitro. J Clin Laser Med Surg. Dec. 2002;20(6):325-33. doi: 10.1089/104454702320901116. PMID: 12513919.—Abstract (Year: 2002).*
(Continued)

*Primary Examiner* — Jonathan T Kuo
*Assistant Examiner* — Vynn V Huh

(57) ABSTRACT

The present invention relates to an oxytocin release stimulation device (10') that can be arranged at or close to skin of a user (40). The oxytocin release stimulation device (10') comprises a lighting unit (14') and a control unit (16"). The control unit (16") controls the lighting unit (14') such that the lighting unit (14') provides light with specific wavelengths and radiant exposures to the skin of the user (40) for a duration that ensures stimulation of a release of oxytocin. Release of oxytocin allows to stimulate a milk ejection reflex and thus to support milk extraction, e.g. when the oxytocin release stimulation device (10) is used with a breast pump (100'). The oxytocin release stimulation device (10') can furthermore allow to reach an oxytocin level during pregnancy that allows to reduce the risk of postpartum depression or that allows to facilitate induction of labor.

13 Claims, 6 Drawing Sheets

(52) U.S. Cl.
CPC ..... *A61N 5/0613* (2013.01); *A61M 2205/052* (2013.01); *A61N 2005/0626* (2013.01); *A61N 2005/0653* (2013.01); *A61N 2005/0659* (2013.01); *A61N 2005/0662* (2013.01)

(58) Field of Classification Search
CPC .... A61N 2005/0659; A61N 2005/0662; A61N 2005/0626; A61N 2005/0644; A61N 2005/0651; A61N 2005/0653; A61N 5/0616; A61N 5/06–2005/073; A61B 2018/00791; A61B 18/20–18/28
USPC .................................................. 607/88–94
See application file for complete search history.

(56) References Cited

FOREIGN PATENT DOCUMENTS

| | | |
|---|---|---|
| EP | 2277571 | 1/2011 |
| EP | 2606816 | 6/2013 |
| KR | 20170026841 | 3/2017 |
| WO | 2010/029483 | 3/2010 |
| WO | 2016126984 | 8/2016 |
| WO | 2017/080851 | 5/2017 |

OTHER PUBLICATIONS

International Search Report and Written Opinion dated Apr. 2, 2019 For International Application No. PCT/EP2019/052287 Filed Jan. 30, 2019.
Subramanian, et al.: "Gene Set Enrichment Analysis: A Knowledge-Based Approach for Interpreting Genome-Wide Expression Profiles", Proceedings of the National Academy of Sciences of the United States of America 2005, 15545.
Liebmann, et al: "Blue-Light Irradiation Regulates Proliferation and Differentiation in Human Skin Cells", J Invest Dermatol. Jan. 2010;130(1):259-69.
https://www.genome.jp/kegg-bin/show_pathway?map=hsa04921 &show_description=show "Oxytocin signaling pathway", Feb. 5, 2019, Kanehisa Laboratories.

* cited by examiner

OXYTOCIN RELEASE STIMULATION

CROSS REFERENCE TO RELATED APPLICATIONS

This application is the U.S. National Phase application under 35 U.S.C. § 371 of International Application No. PCT/EP2019/052287 filed Jan. 30, 2019, published as WO 2019/149774 on Aug. 8, 2019, which claims the benefit of European Patent Application Number 18155117.7 filed Feb. 5, 2018. These applications are hereby incorporated by reference herein.

FIELD OF THE INVENTION

The present invention relates to an oxytocin (OXT) release stimulation device, a breast pump with an OXT release stimulation device, a method for operating a breast pump with an OXT release stimulation device, and a computer program.

BACKGROUND OF THE INVENTION

OXT is one of the neuropeptides normally produced in the supraoptic and paraventricular nuclei of hypothalamus and is secreted from the posterior pituitary into blood. OXT plays a major role in sexual reproduction and during and after labor. In particular OXT supports bonding with a baby, as well as milk ejection from a breast of a mother and may facilitate labor by stimulating uterine contractions.

To start milk ejection from the breast, the milk ejection reflex (MER) also called let-down reflex has to be triggered. OXT induces contraction of smooth muscle during breastfeeding leading to the MER. The main physiological trigger for OXT production is nipple stimulation from suckling action of the baby, i.e. applying positive and negative pressure to a nipple of the breast. Other conditioned stimuli such as baby crying, seeing the baby, and skin contact with the baby support OXT production and thus triggering the MER. A conventional breast pump can stimulate the MER by mimicking the suckling pattern of the baby mechanically, i.e., performing cycles of suction and release by applying cycles of alternating increased pressure and reduced pressure.

WO 2017/080851 A1 shows a breast shield arrangement for a breast pump comprising a breast shield and a sensor. The sensor transmits an input signal into the breast and receives a corresponding reception signal in response that indicates changes in milk flow in the breast. The sensor can be a photoplethysmographic sensor with a light emitting diode (LED) that emits light which is introduced into breast tissue and a detector that receives light reflected in the breast tissue. The amount of reflected light will vary with varying degree of fluid contents in the breast tissue and allows to detect a milk flow in the breast tissue by a change in fluid contents of the breast tissue. The breast pump offers by use of the sensor a direct detection of the start of the milk ejection in the breast tissue even before the milk ejection outside the breast is detected. Thus suction modus of the breast pump can be changed in dependence of the detection of milk ejection.

SUMMARY OF THE INVENTION

It can be seen as an object of the present invention to provide an OXT release stimulation device, a breast pump with an OXT release stimulation device, a method for operating a breast pump with an OXT release stimulation device, and a computer program, which allow to stimulate release of OXT.

In a first aspect of the present invention an OXT release stimulation device is presented. The OXT release stimulation device is configured to be arranged at or close to skin of a user. The OXT release stimulation device comprises a lighting unit and a control unit. The lighting unit is configured for emitting light with a wavelength between 430 nm and 470 nm with a radiant exposure between 0.1 $J/cm^2$ and 100 $J/cm^2$, with a wavelength between 490 nm and 520 nm with a radiant exposure between 0.1 $J/cm^2$ and 100 $J/cm^2$, with a wavelength between 630 nm and 670 nm with a radiant exposure between 0.1 $J/cm^2$ and 300 $J/cm^2$, with a wavelength between 830 nm and 870 nm with a radiant exposure between 0.1 $J/cm^2$ and 300 $J/cm^2$, or with a combination thereof. The control unit is configured for controlling the lighting unit such that the light is provided to the skin of the user for a duration that ensures stimulation of a release of OXT.

The radiant exposure can also be between 0.1 $J/cm^2$ and 100 $J/cm^2$ or for example between 2 $J/cm^2$ and 30 $J/cm^2$ for each of the wavelengths. This allows an improved stimulation of the release of OXT. In a preferred embodiment the light can be light with a wavelength between 430 nm and 470 nm with a radiant exposure between 0.1 $J/cm^2$ and 50 $J/cm^2$, with a wavelength between 490 nm and 520 nm with a radiant exposure between 0.1 $J/cm^2$ and 50 $J/cm^2$, with a wavelength between 630 nm and 670 nm with a radiant exposure between 0.1 $J/cm^2$ and 50 $J/cm^2$, with a wavelength between 830 nm and 870 nm with a radiant exposure between 0.1 $J/cm^2$ and 30 $J/cm^2$, or with a combination thereof.

The lighting unit can comprise a lighting element for emitting the light, such as an LED, an organic light emitting diode (OLED), a laser, a laser diode, a lamp with one or more filters, or a combination thereof. The lighting element can comprise one or more LEDs, one or more OLEDs, one or more lasers, one or more laser diodes, one or more lamps with one or more filters, or a combination of LEDs, OLEDs, lasers, laser diodes, and lamps with filters. The lighting element can for example comprise a series or an array of LEDs, OLEDs, laser diodes, or lamps with one or more filters. This allows to provide light with a narrow range of wavelengths and radiant exposures to the skin of the user. Furthermore LEDs, OLEDs, lasers, and laser diodes allow an efficient usage of energy.

The lighting unit can be configured for emitting the light with a specific wavelength, a range of wavelengths or ranges of wavelengths. Light with a specific wavelength is light with a wavelength of a specific number of nm and a tolerance of 0.5 nm above and below that wavelength, e.g. light with 450 nm corresponds to a wavelength of 449.5 nm to 450.5 nm. Light with a range of wavelengths is light with wavelengths in a range of nm, e.g., light with 440 nm to 450 nm. Light with ranges of wavelengths is light with wavelengths in more than one range of nm, e.g., light with 440 nm to 450 nm together with 460 nm to 470 nm and 850 nm to 860 nm. The lighting unit can be configured for emitting the wavelength, range of wavelengths or ranges of wavelengths simultaneously or consecutively.

Light at specific wavelengths or a specific range or specific ranges of wavelengths increases the relative metabolic activity and triggers a cascade of events leading to increase in OXT level in blood. One example cascade is an increase of adenosine triphosphate (ATP) in the skin from the exposure to blue light. The increase of ATP in the skin triggers release of OXT from epidermal keratinocytes. Experimental measurements using in vitro culture of primary adult human skin cells showed an impact of light on OXT signaling pathways.

Transcriptome of the skin cells including epidermal keratinocytes and dermal fibroblasts was analyzed using gene set enrichment analysis (GSEA) where expression of 24000 genes was tested using Affymetrix platform, one of the standard micro-array techniques. GSEA is described in Subramanian et al., Proceedings of the National Academy of Sciences of the United States of America 2005, 15545 which is incorporated herein by reference. An increase of mRNA level of certain genes including OXT was measured. Increase in mRNA means that a gene that is coding a certain peptide or protein is expressed. Analysis of transcriptome of human epidermal keratinocytes and dermal fibroblasts demonstrated upregulation of OXT signaling pathways and phosphatidylinositol signaling system which regulates OXT. Tables 1 and 2 show maximum values of normalized enrichment scores (NES) for different wavelengths and radiant exposures in $J/cm^2$ after light exposure within 24 hours. Positive NES values mean that the pathway is upregulated. This allows to derive an increase of the release of OXT for example for light with a wavelength of 450 nm with radiant exposure of 2 $J/cm^2$, 10.4 $J/cm^2$, 30 $J/cm^2$ and 41.4 $J/cm^2$, for light with a wavelength of 650 nm with radiant exposure of 30 $J/cm^2$, and for light with a wavelength of 850 nm with radiant exposure of 20 $J/cm^2$ and 30 $J/cm^2$ for an exposure duration of between 30 seconds and 30 minutes (cf. Table 1 and Table 2).

TABLE 1

OXT signaling pathways

|  | 450 nm | 450 nm | 450 nm | 650 nm | 850 nm |
|---|---|---|---|---|---|
| $J/cm^2$ | 2 | 10.4 | 41.4 | 30 | 20 |
| maxNES | 1.19 | 0.95 | 0.96 | 0.67 | 1.16 |

TABLE 2

Phosphatidylinositol signaling system

|  | 450 nm | 450 nm | 850 nm |
|---|---|---|---|
| $J/cm^2$ | 2 | 30 | 30 |
| maxNES | 0.96 | 1.2 | 1.19 |

The NES is the primary statistic for examining gene set enrichment results. By normalizing the enrichment score (ES), GSEA accounts for differences in gene set size and in correlations between gene sets and expression dataset; therefore, the NES can be used to compare analysis results across gene sets. GSEA determines NES as follows:

$$NES = \frac{actual\ ES}{mean\ (ESs\ against\ all\ permutations\ of\ the\ dataset)}.$$

The ES reflects the degree to which a gene set is overrepresented at the top or bottom of a ranked list of genes. GSEA calculates the ES by walking down the ranked list of genes, increasing a running-sum statistic when a gene is in the gene set and decreasing it when it is not. The magnitude of the increment depends on the correlation of the gene with the phenotype. The ES is the maximum deviation from zero encountered in walking the list. A positive ES indicates gene set enrichment at the top of the ranked list; a negative ES indicates gene set enrichment at the bottom of the ranked list.

The light of the specific wavelengths furthermore allows an upregulation of the expression of genes encoding proopiomelanocortin (POMC), Opioid Receptor Kappa 1 (OPRK1), and Cannabinoid Receptor 2 (CNR2). POMC, OPRK1, and CNR2 encode proteins which play a role in analgesic effect and a feeling of euphoria. An increased level of POMC, OPRK1, and CNR2 can allow the user to relax.

The release of OXT into blood, resulting from light stimulation of the skin cells, differs from the release of OXT from the brain into blood, in so far that providing the skin with light of the specific wavelengths or wavelength ranges stimulates a local release of OXT from the epidermal keratinocytes and thus a cutaneous release of OXT.

Since the control unit is configured for controlling the lighting unit such that the light is provided to the skin of the user with the specific wavelength, wavelength range or wavelength ranges for a duration that ensures stimulation of a release of OXT, release of OXT can be stimulated easily by the user using the OXT stimulation release device without further knowledge. OXT release allows to stimulate the MER. This can allow supporting milk extraction, e.g., when the OXT release stimulation device is used with a breast pump for extracting milk. The OXT release stimulation device allows to stimulate cutaneous release of OXT which allows to reach a level of OXT above a threshold of OXT that is for example sufficient to trigger the MER, to add the cutaneously released OXT to the OXT released from the brain to reach the level above the threshold, and/or to maintain the level of OXT above the threshold for a longer period of time. The OXT release stimulation device uses light of specific wavelengths or respectively so called photobiomodulation to stimulate the release of OXT. The OXT release stimulation device can allow to support preserving milk volume by supporting milk extraction with a breast pump for extracting milk. The OXT release stimulation device allows to support extraction of milk in a stressful environment when stress hinders release of OXT from the hypothalamus. Furthermore an OXT threshold level can be reached during pregnancy that allows to reduce the risk of postpartum depression (PPD) or that allows to facilitate induction of labor.

The control unit can be configured to ensure that the light provided to skin of the user is provided to hairy skin of the user. This allows an improved stimulation of the release of OXT.

In one embodiment the duration for providing the light to the skin of the user in order to stimulate a release of OXT is at least 30 seconds. This allows to ensure stimulation of the release of OXT and a sufficient amount of OXT released for triggering the MER. The duration can for example be between 30 seconds and 30 minutes. This allows to perform a milk extraction session with stimulated MER. In other embodiments the duration for providing the light to the skin of the user in order to stimulate a release of OXT can be longer, e.g., for long term increase of OXT for reducing the risk of PPD or for increasing OXT level for facilitating induction of labor. While for reducing the risk of PPD the OXT level shall not be significantly increased, the increase of OXT level for facilitating induction of labor is higher than for reducing the risk of PPD.

The lighting unit can be configured for emitting the light as continuous wave (cw) or in a pulsed mode (pm). This allows to provide light to the skin of the user with various operation modes in order to optimize the OXT release. Using different wavelengths in different operation modes can allow to stimulate the release of OXT in different signaling pathways and for different durations. Using pm for stimulation with light allows an efficient usage of energy and an efficient stimulation.

The OXT release stimulation device can comprise an attachment unit. The attachment unit can be configured for attaching the lighting unit at or close to the skin of the user in order to provide the light to the skin of the user. This allows the lighting unit to be close to the skin of the user in order to provide a majority of the emitted light to the skin of the user, i.e. improving the energy efficiency as a majority of emitted light is provided to the skin. The attachment unit can be a garment, such as a band, a wristband, a headband, a watch, a sock, a glove, a bra, or any other kind of garment worn by the user. The garment as part of the OXT release stimulation device can be worn instead of other garments usually worn by the user. This allows attaching the OXT release stimulation device at the skin of the user for long durations, such as during a day and without requiring an additional device that may disturb the user. Alternatively the attachment unit can for example be a pillow, such as a neck pillow or the like that can be attached to the user's body for example during a milk extraction session. This allows a double use of the pillow for holding the user and stimulating the release of OXT. The lighting unit can be configured to direct light toward the skin of the user in order to stimulate the release of OXT from the skin to the blood stream.

The lighting unit can be configured to provide the light to the skin of the breast of the user. Directly stimulating the breast of the user with the light allows to have a local cutaneous release of OXT at the breast of the user which allows an improved stimulation of the MER. The lighting unit can be configured to direct light toward the skin of the breast of the user in order to stimulate the release of OXT from the skin of the breast of the user. Alternatively or additionally the lighting unit can be configured to provide the light to the skin of any other part of the body of the user, e.g., to a hand, a wrist, an arm, a neck, or a back of the user.

The lighting unit can be configured to be arranged at the breast of the user, e.g. via the attachment unit or via incorporating the lighting unit or parts of the lighting unit in a breast shield. The attachment unit can also for example be a suction pad. This allows attaching the lighting unit directly at the breast of the user.

The OXT release stimulation device can comprise a massage unit. The massage unit can be configured to be arranged at the skin of the user, for example at the breast, hand, wrist, arm, neck or back of the user. The massage unit can furthermore be configured to perform cutaneous tactile stimulation to the skin of the user in order to stimulate release of OXT. This allows a synergetic effect with light stimulation as release of OXT can be increased. The massage unit can comprise a collapsible membrane, a pneumatic chamber, a brush, or any other mechanical means for performing cutaneous tactile stimulation to the skin of the user. The control unit can be configured to control the massage unit. The memory of the control unit can comprise massaging parameters, such as a frequency and intensity of the massage. The massage unit can for example be arranged at a breast shield.

The oxytocin release stimulation device can be configured for providing the light to the skin of the user as a combination of a wavelength between 430 nm and 470 nm with a radiant exposure between 0.1 J/cm$^2$ and 100 J/cm$^2$, a wavelength between 490 nm and 520 nm with a radiant exposure between 0.1 J/cm$^2$ and 100 J/cm$^2$, a wavelength between 630 nm and 670 nm with a radiant exposure between 0.1 J/cm$^2$ and 300 J/cm$^2$, and a wavelength between 830 nm and 870 nm with a radiant exposure between 0.1 J/cm$^2$ and 300 J/cm$^2$ in order to stimulate MER, for providing the light to the skin of the user with alternating wavelengths once MER has been triggered, or for providing the light to the skin of the user as a combination of the wavelengths in order to stimulate MER and with alternating wavelengths once MER has been triggered. The light can be a combination of any two or more of the wavelengths or wavelength ranges. Using light with a combination of the wavelengths allows an efficient stimulation of the OXT release. Using alternating wavelengths allows to avoid saturation. The OXT release stimulation device can also be configured for providing the light to the skin of the user as a combination of a wavelength between 430 nm and 470 nm with a radiant exposure between 0.1 J/cm$^2$ and 50 J/cm$^2$, a wavelength between 490 nm and 520 nm with a radiant exposure between 0.1 J/cm$^2$ and 50 J/cm$^2$, a wavelength between 630 nm and 670 nm with a radiant exposure between 0.1 J/cm$^2$ and 50 J/cm$^2$, and a wavelength between 830 nm and 870 nm with a radiant exposure between 0.1 J/cm$^2$ and 30 J/cm$^2$ in order to stimulate MER, for providing the light to the skin of the user with alternating wavelengths once MER has been triggered, or for providing the light to the skin of the user as a combination of the wavelengths in order to stimulate MER and with alternating wavelengths once MER has been triggered. The control unit can be configured for performing a wavelength combination operation mode in order to control the lighting unit for providing the light to the skin of the user as a combination of the wavelengths and a wavelength alternating operation mode in order to control the lighting unit for providing the light with alternating wavelengths.

The lighting unit can comprise a light source and a light delivery unit. The light source is configured for generating the light. The lighting element of the lighting unit can for example be part of the light source of the lighting unit in order to generate the light. The light delivery unit is configured for providing the light to the skin of the user. At least the light delivery unit can be configured to be arranged at or close to the skin of the user in order to provide the light to the skin of the user. The light delivery unit can be configured to be arranged at or close to the skin of the user or the light source and the light delivery unit can be configured to be arranged at or close to the skin of the user. The attachment unit can be configured for attaching the light delivery unit or the light source and the light delivery unit at or close to the skin of the user in order to provide the light to the skin of the user. The light delivery unit is connected with the light source, such that the light delivery unit can provide light generated by the light source to the skin of the user. The light delivery unit and the light source can for example be connected via an optical connection such as one or more optical fibers. The light delivery unit can also include the optical connection. The light delivery unit can for example include one or more optical fibers.

The light delivery unit can be arranged in or on a breast shield, such as inside of the breast shield material or on an inner side of the breast shield which is in contact with the skin of the breast of the user when the breast shield received a breast of the user or on an outer side of a breast shield opposite of the inner side. If the lighting unit is arranged in a breast shield or on the outer surface of a breast shield, the respective breast shield is translucent for the light provided by the lighting unit, in order to allow the light of the lighting unit to be transmitted to the breast of the user. Alternatively the light delivery unit and the light source can be arranged in or on a breast shield, such as inside of the breast shield material or on an inner side or on an outer side of a breast shield.

The control unit can be configured to transmit control signals to the lighting unit in order to control light parameters of the light emitted by the lighting unit. Light parameters can for example be the wavelength, range of wavelengths, ranges of wavelengths, wavelength dependent irradiance, wavelength dependent duration of exposure and/ or wavelength dependent radiant exposure. The irradiance together with duration of exposure determines the radiant exposure. The control unit can be configured to change between light with cw and light in pm. The control unit can be configured to adjust pulse parameters of pulses of light in the pm, such as pulse width, pulse frequency, pulse shape, or the like. The control unit can comprise a processor for processing data. The control unit can comprise a memory. The memory can be configured to store the lighting parameters and predetermined operation modes. The control unit can be configured to perform the predetermined operation modes, such as a MER stimulation mode in which light with predetermined wavelength, range of wavelengths, or ranges of wavelengths is provided to the skin of the user in order to initially stimulate the MER or a MER prolonging mode in which light with predetermined wavelength, range of wavelengths, or ranges of wavelengths is provided to the skin of the user in order to prolong the MER. Other operation modes include cw operation mode and pm operation mode. The control unit can for example control the lighting unit based on different light parameters in the different operation modes.

The control unit can comprise a user interface for allowing user interaction. The user interface can be configured to receive user input, e.g. selection or adjustment of the light parameters and to generate control signals based on the user input. The control unit can be configured to transmit the control signals to the lighting unit in order to control the lighting unit. The user interface can be configured to provide the user a choice of the different operation modes or the control unit can automatically perform different operation modes. The control unit can for example comprise sensors and determine an operation mode based on sensor data received from the sensors.

The control unit can be configured to activate the lighting unit. The control unit can for example be configured to activate the lighting unit when the lighting unit is close to or at the skin of the user, e.g., when the breast of the user is received in a breast shield with the lighting unit. Alternatively or additionally the control unit can be configured to activate the lighting unit when a control signal provided by the user interface is received. The control unit can be configured to deactivate the lighting unit. The control unit can for example be configured to deactivate the lighting unit when the lighting unit is not close to or not at the skin of the user, e.g., when the breast of the user is removed from a breast shield with the lighting unit. Alternatively or additionally the control unit can be configured to deactivate the lighting unit when a control signal for deactivating the lighting unit provided by the user interface is received. The control unit can for example be configured to activate the lighting unit in advance of a milk extraction session, e.g., below 30 minutes, such as 10 minutes before milk extraction is started. This allows to increase the OXT level above the threshold level for triggering the MER and allows supporting the MER. The control unit allows control of the OXT release stimulation device.

The OXT release stimulation device can comprise a power source. The power source can be configured for powering the lighting unit, the control unit, the massage unit, or any combination of them. The power source can for example be a battery. This allows mobile use of the OXT release stimulation device.

In a further aspect of the present invention a breast pump is presented. The breast pump comprises an OXT release stimulation device according to any of the claims 1 to 8 or any embodiment of the OXT release stimulation device, a breast shield, and a pressure source. The breast shield is configured for receiving a breast of the user therein. The pressure source is in air-ducting connection to the breast shield for generating cycles of alternating increased pressure and reduced pressure in the breast shield to extract milk from the breast of the user.

The breast shield has a shape that is configured to receive the breast of the user. The breast shield can for example be funnel shaped. The breast shield can be made from a resilient material such as polyurethane or silicone. This allows a better fit to the breast of the user and is more comfortable.

The pressure source can be a manually operated pump or an automatic pressure source, such as an electric vacuum pump. This allows to express milk from the breast of the user.

The control unit of the OXT release stimulation device can be configured to control the pressure source. Alternatively or additionally the breast pump can comprise a breast pump control unit for controlling the pressure source and/or the control unit of the OXT release stimulation device. The breast pump control unit can comprise a user interface for user interaction. This allows central control of all components of the breast pump via the breast pump control unit.

The breast pump can comprise a breast unit and a base unit. The breast unit can comprise the breast shield. The breast unit can be configured to be arranged at the breast of the user. The base unit can comprise the pressure source, a power supply, or the pressure source and the power supply. The power supply is configured for providing power. The breast unit and the base unit are connected via a connection line. The connection line can comprise an air-duct, a power line, an optical connection, or any combination of them.

The power line can be a power cord connected from the base unit of the breast pump to the breast unit in order to supply power to the breast unit. Alternatively or additionally the breast unit can be powered by the power source of the OXT release stimulation device. The light source can be included in the base unit or the breast unit. The light source can be detachable from the base unit. This allows to use the OXT release stimulation device independent of the breast pump and thus to stimulate release of OXT using the OXT release stimulation device in order to prepare the breast of the user for breast feeding or milk extraction before a milk extraction session, e.g. below 30 minutes, such as below 10 minutes, before starting milk extraction.

The breast unit can comprise a container for storing expressed milk. The breast unit can comprise a breast shield connector for connecting the breast shield with the container.

The OXT release stimulation device can be connected to or can be part of any suitable breast pump.

In a further aspect of the present invention a use of light for stimulating a release of OXT from skin of a user is presented. The used light has a wavelength between 430 nm and 470 nm with a radiant exposure between 0.1 J/cm$^2$ and 100 J/cm$^2$, a wavelength between 490 nm and 520 nm with a radiant exposure between 0.1 J/cm$^2$ and 100 J/cm$^2$, a wavelength between 630 nm and 670 nm with a radiant exposure between 0.1 J/cm$^2$ and 300 J/cm$^2$, a wavelength between 830 nm and 870 nm with a radiant exposure between 0.1 J/cm$^2$ and 300 J/cm$^2$, or a combination thereof. The light is provided to the skin of the user for stimulating the release of OXT. The light can be provided as cw or in pm.

In one embodiment light with a wavelength between 430 nm and 470 nm with a radiant exposure between 0.1 J/cm$^2$ and 50 J/cm$^2$, light with a wavelength between 490 nm and 520 nm with a radiant exposure between 0.1 J/cm$^2$ and 50 J/cm$^2$, light with a wavelength between 630 nm and 670 nm with a radiant exposure between 0.1 J/cm$^2$ and 50 J/cm$^2$, light with a wavelength between 830 nm and 870 nm with a radiant exposure between 0.1 J/cm$^2$ and 30 J/cm$^2$, or a combination thereof is provided to the skin of the user for stimulating the release of OXT.

In a further aspect of the present invention a method for operating the breast pump according to claim 9 or any embodiment of the breast pump is presented. The method comprises the steps:
  receiving the breast of the user in the breast shield,
  emitting the light with a wavelength between 430 nm and 470 nm with a radiant exposure between 0.1 J/cm$^2$ and 100 J/cm$^2$, with a wavelength between 490 nm and 520 nm with a radiant exposure between 0.1 J/cm$^2$ and 100 J/cm$^2$, with a wavelength between 630 nm and 670 nm with a radiant exposure between 0.1 J/cm$^2$ and 300 J/cm$^2$, with a wavelength between 830 nm and 870 nm with a radiant exposure between 0.1 J/cm$^2$ and 300 J/cm$^2$, or a combination thereof, and
  providing that the emitted light is provided to the skin of the user for a duration that ensures that release of OXT is stimulated. This allows to stimulate the release of OXT.

The light can also be emitted with a radiant exposure between 0.1 J/cm$^2$ and 100 J/cm$^2$, for example with a radiant exposure between 2 J/cm$^2$ and 30 J/cm$^2$, for each of the wavelengths. In one embodiment of the method the light is emitted with a wavelength between 430 nm and 470 nm with a radiant exposure between 0.1 J/cm$^2$ and 50 J/cm$^2$, a wavelength between 490 nm and 520 nm with a radiant exposure between 0.1 J/cm$^2$ and 50 J/cm$^2$, a wavelength between 630 nm and 670 nm with a radiant exposure between 0.1 J/cm$^2$ and 50 J/cm$^2$, a wavelength between 830 nm and 870 nm with a radiant exposure between 0.1 J/cm$^2$ and 30 J/cm$^2$, or a combination thereof.

The method can comprise the step:
  generating cycles of alternating increased pressure and reduced pressure in the breast shield to extract milk from the breast of the user.

Alternatively or additionally the method can comprise the step:
  massaging the skin of the user in order to stimulate release of OXT.

The skin of the breast or any other body part of the user can be massaged. Preferably the massaged skin is hairy skin. The massaging can be performed manually or by a massaging unit included in the OXT release stimulation device of the breast pump.

In a further aspect of the invention a method for operating the OXT release stimulation device for stimulating release of OXT is presented. The method comprises the steps:
  arranging the OXT release stimulation device such that the lighting unit provides light to the skin of the user, and
  emitting the light with a wavelength between 430 nm and 470 nm with a radiant exposure between 0.1 J/cm$^2$ and 100 J/cm$^2$, with a wavelength between 490 nm and 520 nm with a radiant exposure between 0.1 J/cm$^2$ and 100 J/cm$^2$, with a wavelength between 630 nm and 670 nm with a radiant exposure between 0.1 J/cm$^2$ and 300 J/cm$^2$, with a wavelength between 830 nm and 870 nm with a radiant exposure between 0.1 J/cm$^2$ and 300 J/cm$^2$, or a combination thereof, and
  providing that the emitted light is provided to the skin of the user for a duration that ensures that release of OXT is stimulated.

The method can comprise the step arranging the OXT release stimulation device such that the lighting unit provides light to the skin of the breast of the user. This allows to stimulate local cutaneous release of OXT in the breast of the user. Local cutaneous release of OXT in the breast of the user can allow to improve stimulation of the MER. The method for operating the OXT release stimulation device can be incorporated in a computer program.

In a further aspect of the present invention a computer program for operating a breast pump according to claim 9 or any embodiment of the breast pump is presented. The computer program comprises program code means for causing a processor to carry out the method as defined in claim 12 or any embodiment of the method, when the computer program is run on the processor.

In a further aspect a computer readable medium having stored the computer program of claim 14 is presented. Alternatively or additionally the computer readable medium can have the computer program according to any embodiment of the computer program stored.

It shall be understood that the OXT release stimulation device of claim 1, the breast pump of claim 9, the method of claim 12, the computer program of claim 14, and the computer readable medium of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
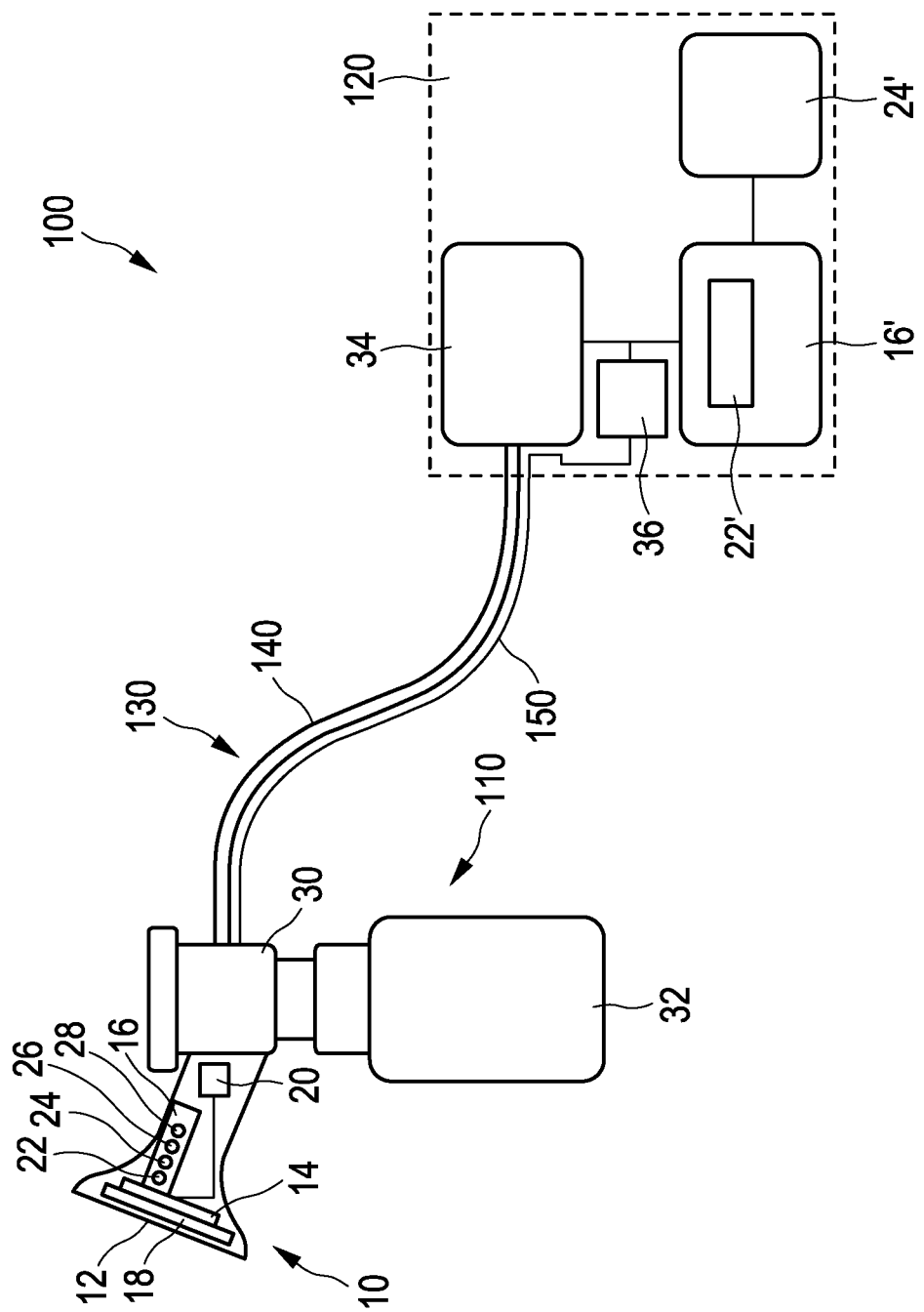
FIG. 1 shows schematically and exemplarily a first embodiment of an OXT release stimulation device in a first embodiment of a breast pump.

FIG. 1 shows schematically and exemplarily a first embodiment of an OXT release stimulation device 10 in a first embodiment of a breast pump 100. The OXT release stimulation device 10 can be used for stimulating the release of OXT and the MER. The breast pump 100 can be used for extracting milk from a breast of a user. The breast pump 100 comprises a breast unit 110 and a base unit 120. The breast unit 110 and the base unit 120 are connected via connection line 130. The breast unit 110 comprises the OXT release stimulation device 10 and can be arranged at the breast of the user.

The OXT release stimulation device 10 comprises a breast shield 12, a lighting unit in form of LED module 14, a control unit 16, a massage unit in form of a collapsible membrane 18, and a power source in form of a battery 20. In other embodiments the lighting unit can for example be a laser module, laser diode module or any other module configured for emitting light with specific wavelengths and radiant exposures that allow to stimulate the release of OXT. The laser module can comprise a laser for emitting light and the laser diode module can comprise one or more laser diodes, e.g. an array of laser diodes. In other embodiments the massage unit can comprise or be any other unit for performing cutaneous tactile stimulation to the breast of the user, e.g. a pneumatic chamber, a brush or any other mechanical means for performing cutaneous tactile stimulation to the skin of the user. In other embodiments the OXT release stimulation device can be detachable from the breast shield and/or the breast shield can be a part of the breast pump. The breast shield is an optional part of the OXT release stimulation device. In other embodiments the breast shield can for example be replaced by a garment or a pillow.

The breast shield 12 is funnel shaped and receives the breast of the user therein. The breast shield 12 in this embodiment is made from polyurethane. In other embodiments the breast shield can have any other shape that allows to receive the breast and furthermore can also be made from any other resilient material, e.g. from silicone.

The LED module 14 comprises an array of LEDs incorporated in the breast shield 12. In other embodiments the lighting unit can be detachable from the breast shield or can be separately attached on to the breast of the user, e.g. via an attachment unit such as a suction pad. The LEDs provide light to skin of the breast of the user received in the breast shield 12 in order to stimulate release of OXT. The breast shield 12 is transparent for the light provided by the LEDs. In this embodiment, the light provided to the skin of the breast is light with a wavelength between 430 nm and 470 nm with a radiant exposure between 0.1 J/cm$^2$ to 50 J/cm$^2$, with a wavelength between 490 nm and 520 nm with a radiant exposure between 0.1 J/cm$^2$ and 50 J/cm$^2$, with a wavelength between 630 nm and 670 nm with a radiant exposure between 0.1 J/cm$^2$ and 50 J/cm$^2$, with a wavelength between 830 nm and 870 nm with a radiant exposure between 0.1 J/cm$^2$ and 30 J/cm$^2$, or a combination thereof. The radiant exposures can be different in other embodiments, e.g. between 0.1 J/cm$^2$ and 100 J/cm$^2$, such as between 2 J/cm$^2$ and 30 J/cm$^2$, for each of the wavelengths. In one embodiment the light is light with a wavelength between 430 nm and 470 nm with a radiant exposure between 0.1 J/cm$^2$ and 100 J/cm$^2$, with a wavelength between 490 nm and 520 nm with a radiant exposure between 0.1 J/cm$^2$ and 100 J/cm$^2$, with a wavelength between 630 nm and 670 nm with a radiant exposure between 0.1 J/cm$^2$ and 300 J/cm$^2$, with a wavelength between 830 nm and 870 nm with a radiant exposure between 0.1 J/cm$^2$ and 300 J/cm$^2$, or with a combination thereof. The LED module 14 can either provide one wavelength, a range of wavelengths or several ranges of wavelengths each with same or different radiant exposure.

The control unit 16 comprises a processor 22, a user interface in form of a touch display 24, a memory 26, and a sensor in form of a proximity sensor 28. In other embodiments the user interface can also for example be a simple switch, button or any other user interface that allows the user to interact with the OXT release stimulation device. In other embodiments the sensor can also for example be a temperature sensor or any other sensor that allows to detect whether a breast is received in the breast shield. In yet other embodiments the sensor can be any other type of sensor, e.g. a sensor for determining parameters of the skin of the user in order to determine a duration of light stimulation that ensures that release of OXT is stimulated or a sensor for determining whether MER has been triggered.

The control unit 16 controls the operation of the OXT release stimulation device 10 and in particular of the LED module 14 and the collapsible membrane 18. The control unit 16 controls the LED module 14 such that the light is provided to the skin of the breast of the user for a duration that ensures stimulation of a release of OXT.

The processor 22 allows processing of control signals. Control signals can be received from the touch display 24 provided by the user, from the memory 26, or from the proximity sensor 28. Control signals can for example include light parameters, sensor data, massage parameters, or can be simple control signals for activating or deactivating the LED module 14 and/or the collapsible membrane 18.

The memory 26 stores light parameters, massage parameters, operation modes, and a computer program for operating the OXT release stimulation device 10.

The proximity sensor 28 detects when the breast of the user is received in the breast shield 12 and provides a control signal for activating the LED module 14 to the processor 22. The proximity sensor 28 is optional. In other embodiments the OXT release stimulation device does not include a sensor.

The control unit 16 allows to automatically operate the OXT release stimulation device 10 such that the LED module 14 is activated when the breast is received in the breast shield 12. The LED module 14 provides light to the skin of the breast of the user for a duration of at least 30 seconds in order to ensure that release of OXT is stimulated. Typically a milk extraction session takes less than 30 minutes and the LED module 14 provides light for the duration of the milk extraction session. The control unit 16 in this embodiment deactivates the LED module 14 after 30 minutes or when the control unit 16 is provided with a control signal for deactivating the LED module 14. The control signal for deactivating the LED module 14 can be provided from the user via the touch display 24. In other operation modes the LED module 14 can be deactivated after any other duration, e.g. 25 minutes, or only through manual deactivation via the user interface. Furthermore in one operation mode the LED module 14 and the collapsible membrane 18 are operated in parallel in order to stimulate release of OXT.

The collapsible membrane 18 is arranged at the breast of the user, when the breast shield 12 is arranged at the breast and can perform cutaneous tactile stimulation to the breast of the user in order to stimulate release of OXT. The collapsible membrane 18 is controlled by the control unit 16. The frequency and intensity of the cutaneous tactile stimulation to the breast of the user can be controlled via the control unit 16. The massage parameters included in the memory 26 define frequency and intensity of the operation of the collapsible membrane 18. The collapsible membrane 18 is optional. In other embodiments the OXT release stimulation device does not have a massage unit.

The battery 20 powers the LED module 14, the control unit 16, and the collapsible membrane 18. The battery 20 is optional. In other embodiments the OXT release stimulation device 10 is powered solely via connection line 130. In this embodiment battery 20 is rechargeable and can be charged via connection line 130. The battery 20 allows operation of the OXT release stimulation device 10 without a base unit 120, for example using a manual breast pump for manually generating suction in the breast shield (not shown).

In this embodiment the connection line 130 includes an air-duct 140 and a power line in form of power cord 150. The power cord 150 provides power to the LED module 14, the control unit 16, the collapsible membrane 18 and the battery 20. The OXT release stimulation device 10 is connected with the connection line 130 via breast shield connector 30.

The breast shield connector 30 comprises container 32 for storing extracted milk. The breast shield connector 30 and container 32 together with the OXT release stimulation device 10 form the breast unit 110.

The base unit 120 comprises a pressure source in form of a vacuum pump 34, a power supply 36, a breast pump control unit 16', and a user interface in form of an on and off switch 24'.

The vacuum pump 34 is in air-ducting connection via the air-duct 140 to the breast shield 12 for generating cycles of alternating increased pressure and reduced pressure in the breast shield 12 to extract milk from the breast of the user. In other embodiments the vacuum pump can be replaced by any other pressure source that allows generating cycles of alternating increased pressure and reduced pressure. The vacuum pump can for example be replaced by a manual vacuum pump that is operated with a handle. Such a manual vacuum pump can be included in the breast unit and does not require the base unit. This allows improved mobile operation of the embodiment of the breast pump with a manual vacuum pump.

The power supply 36 provides power to the components of the base unit 120 and via the power cord 150 also to the components of the breast unit 110.

The breast pump control unit 16' comprises a processor 22'. The breast pump control unit 16' controls the operation of the vacuum pump 34 and the power supply 36. This allows operating the breast pump 100. In other embodiments the breast pump control unit can also be used for controlling the OXT release stimulation device.

Figure 2:
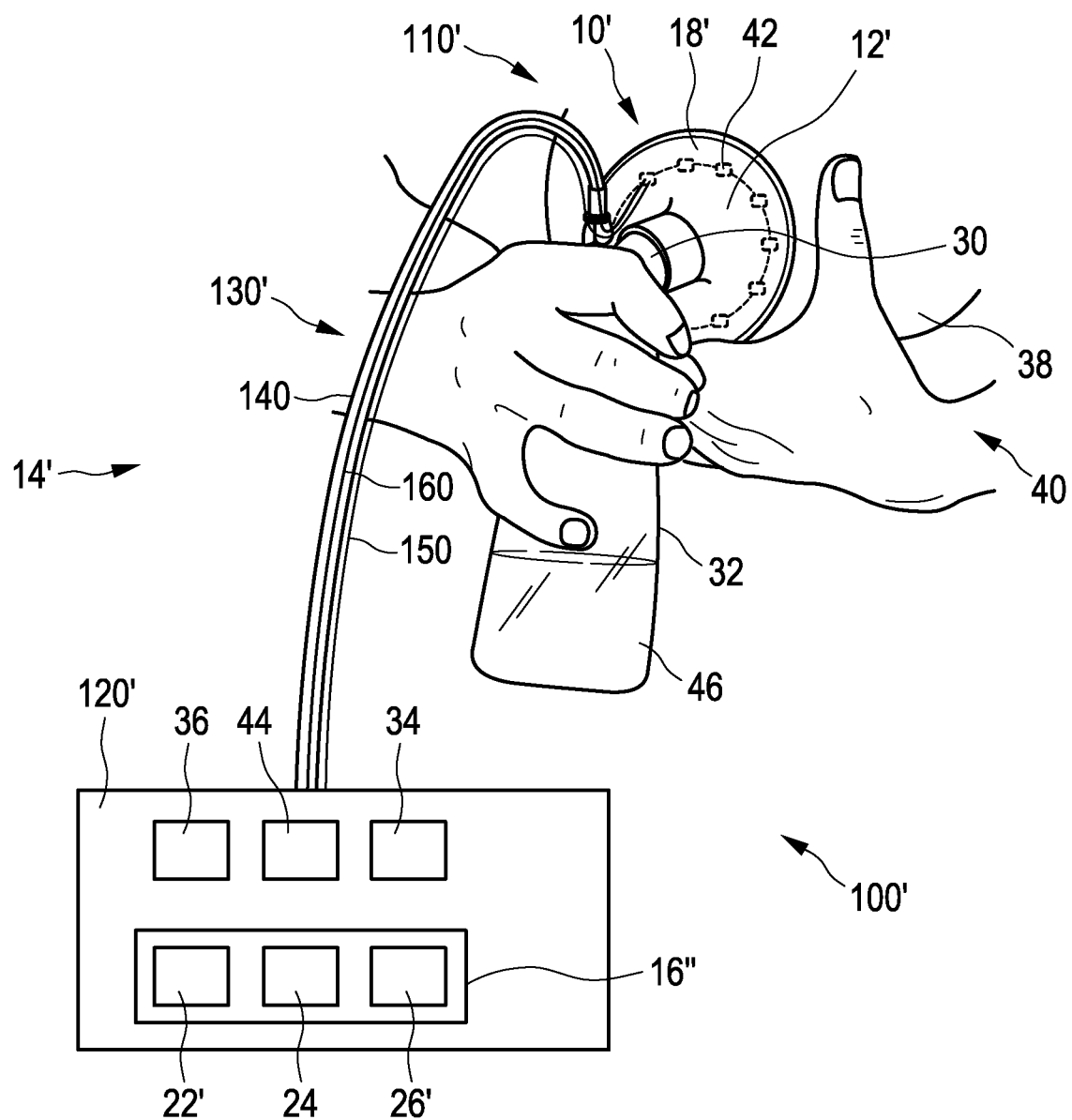
FIG. 2 shows schematically and exemplarily a second embodiment of the OXT release stimulation device in a second embodiment of the breast pump.

FIG. 2 shows schematically and exemplarily a second embodiment of an OXT release stimulation device 10' in a second embodiment of a breast pump 100'. The breast pump 100' comprises breast unit 110' and base unit 120' which are connected via connection line 130'. The connection line 130' comprises air-duct 140, a power line in form of power cord 150, and a bundle of optical fibers 160. The breast unit 110' is arranged at breast 38 of user 40. The breast unit 110' comprises the OXT release stimulation device 10', a breast shield connector 30, and a container 32.

The OXT release stimulation device 10' includes a breast shield 12', a lighting unit 14' with a light delivery unit in form of a mirror arrangement 42 and a light source in form of an LED module 44, a control unit 16", and a massage unit in form of a collapsible membrane 18'.

In the breast shield 12' cycles of alternating increased pressure and reduced pressure are provided to extract milk from the breast 38 of the user 40. Extracted milk 46 is stored in the container 32. The cycles of alternating increased pressure and reduced pressure are provided via the air-duct 140 and the breast shield connector 30 from the base unit 120'. The breast shield 12' is funnel shaped and made from polyurethane. In other embodiments the breast shield can have a different shape and can also be made from a different resilient material, e.g. from silicone. The mirror arrangement 42 and the collapsible membrane 18' are incorporated in the material of the breast shield 12'.

The LED module 44 is arranged in the base unit 120'. The LED module 44 generates light with a wavelength between 430 nm and 470 nm with a radiant exposure between 0.1 J/cm$^2$ and 100 J/cm$^2$, with a wavelength between 490 nm and 520 nm with a radiant exposure between 0.1 J/cm$^2$ and 100 J/cm$^2$, with a wavelength between 630 nm and 670 nm with a radiant exposure between 0.1 J/cm$^2$ and 300 J/cm$^2$, with a wavelength between 830 nm and 870 nm with a radiant exposure of 0.1 J/cm$^2$ and 300 J/cm$^2$, or a combination thereof. The LED module 44 can generate one specific wavelength, a range of wavelengths or several ranges of wavelengths each with same or different radiant exposures. The mirror arrangement 42 and the LED module 44 of the lighting unit 14' are connected via an optical connection in form of optical fibers 160, such that light provided by LED module 44 can be provided to the breast 38 of the user 40 via the mirror arrangement 42. The mirror arrangement 42 is incorporated in the material of the breast shield 12'. The material of the breast shield 12' is transparent for the light provided by the LED module 44.

The collapsible membrane 18' is controlled via control signals provided via the power cord 150 from the base unit 120' and can perform a cutaneous tactile stimulation to the breast 38 of the user 40. The collapsible membrane 18' can contract and expand in dependence of the control signals. The collapsible membrane 18' is optional.

The base unit 120' comprises the control unit 16" of the OXT release stimulation device 10', a vacuum pump 34, a power supply 36, and the LED module 44.

The control unit 16" comprises a processor 22', a user interface in form of a touch display 24, and a memory 26'. The control unit 16" controls the operation of the breast pump 100' and the OXT release stimulation device 10'. The control unit 16" controls the suction pattern provided by the vacuum pump 34, power provided by the power supply 36, and the light provided by the LED module 44. The touch display 24 allows users interaction and manual control of the breast pump 100'. In other embodiments the touch display 24 can be replaced with any other user interface. The memory 26' stores light parameters, massage parameters, operation modes, and a computer program for operating the OXT release stimulation device 10'.

The vacuum pump 34 generates cycles of alternating increased pressure and reduced pressure and provides the cycles of alternating increased pressure and reduced pressure via the air-duct 140 and breast shield connector 30 to the breast shield 12'. In other embodiments the vacuum pump can be replaced by any other pressure source, e.g. a manual handle for providing increased and reduced pressure.

The power supply 36 provides power to the components of the base unit 120' and to the collapsible membrane 18' via the power cord 150.

The operation of the breast pump 100' presented in FIG. 2 is similar to the operation of the breast pump 100 presented in FIG. 1. Breast pump 100' and breast pump 100 both provide light with specific wavelengths and radiant exposures to the skin of the breast 38 of the user 40. However, breast pump 100' and breast pump 100 are different in that the light is generated in the breast unit 110 in the breast pump 100 and in the base unit 120' in the breast pump 100'. The light generated in the base unit 120' is then transmitted via optical fibre 160 to the breast unit 110' and onto the skin of the breast 38 of the user 40.

Figure 3:
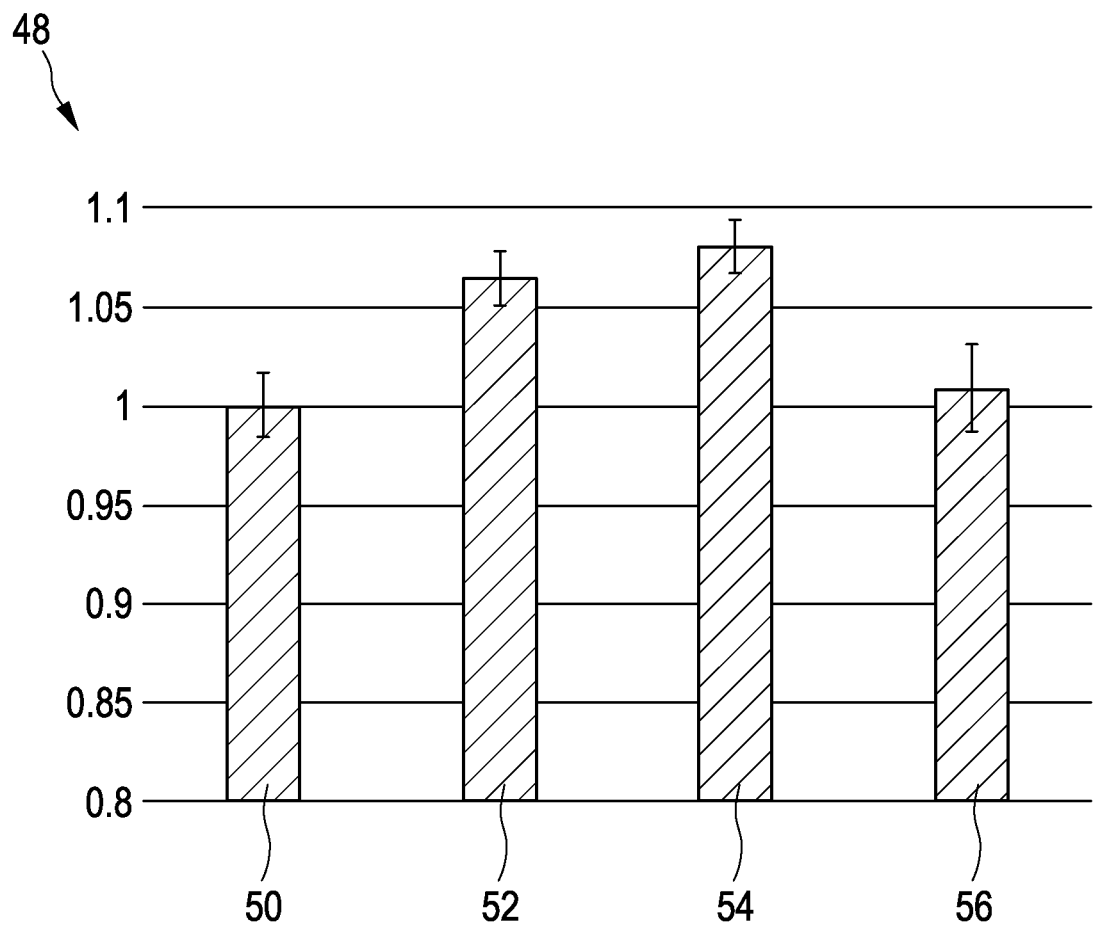
FIG. 3 shows relative metabolic activity in dependence of light with different wavelengths.

FIG. 3 shows relative metabolic activity 48 of human skin cells in dependence of light with different wavelengths and a radiant exposure of 2 J/cm$^2$. The relative metabolic activity 48 is normalized to the metabolic activity for a situation in which no light 50 is provided to the human skin cells. The relative metabolic activity 48 is increased for blue light 52 with a wavelength of 450 nm and for cyan light 54 with a wavelength of 505 nm. For green light 56 with a wavelength of 530 nm no increase of relative metabolic activity is observed, i.e., only specific wavelengths and wavelength ranges in combination with specific radiant exposures result in increased relative metabolic activity 48.

Figure 4:
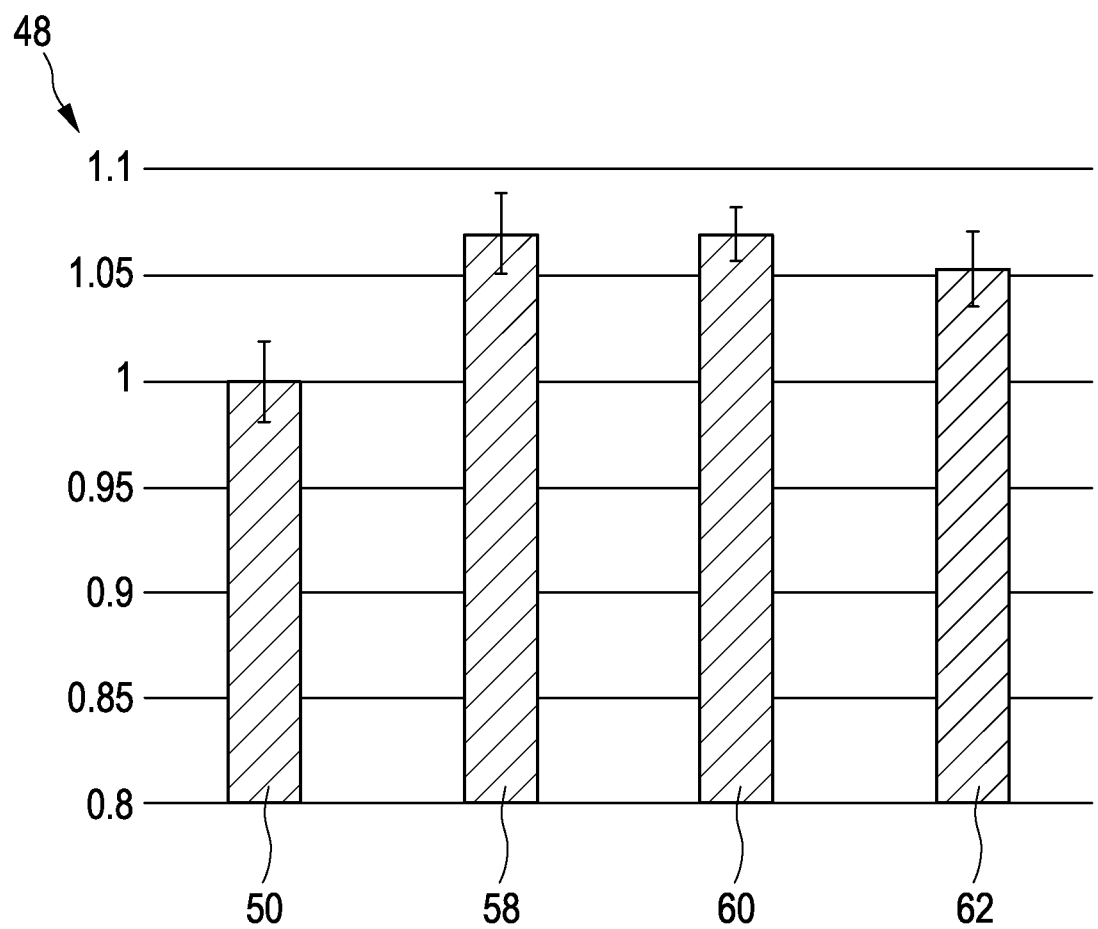
FIG. 4 shows relative metabolic activity in dependence of light with different wavelengths and different radiant exposures.

FIG. 4 shows relative metabolic activity 48 of human skin cells in dependence of light with different wavelengths and different radiant exposures. Relative metabolic activity 48 is increased for red light 58 with a wavelength of 650 nm with a radiant exposure of 3.2 J/cm$^2$, red light 60 with a wavelength of 650 nm with a radiant exposure of 30 J/cm$^2$, and infra-red light 62 with a wavelength of 850 nm with a radiant exposure of 60 J/cm$^2$.

The results presented in FIGS. 3 and 4 together with the experimental results from Tables 1 and 2 allow to conclude that only light with specific parameters, i.e., light with the specific wavelengths and radiant exposures that increase the relative metabolic activity and upregulate the OXT signalling pathways or the phosphatidylinositol signaling system which regulates OXT, lead to a stimulation of the release of OXT.

Figure 5:
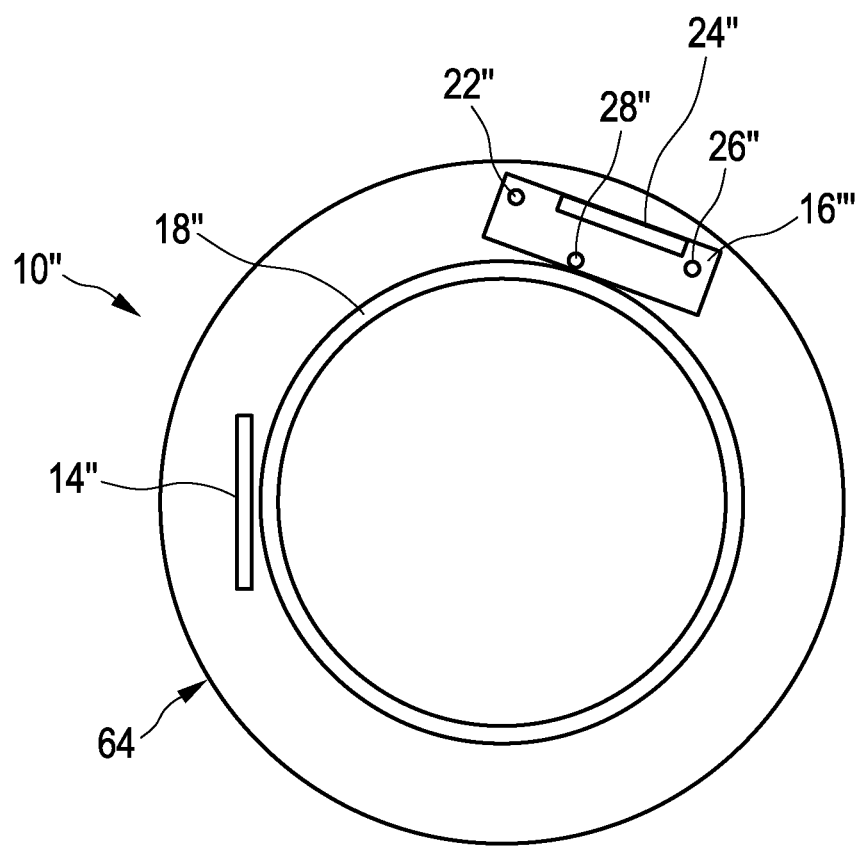
FIG. 5 shows schematically and exemplarily a third embodiment of the OXT release stimulation device with a wristband.

FIG. 5 shows schematically and exemplarily a third embodiment of the OXT release stimulation device 10" with an attachment unit in form of a wristband 64. In other embodiments the attachment unit can also be any other kind of garment worn by the user, such as a headband, a watch, a sock, a glove or a bra. In yet other embodiments the attachment unit can also be a pillow, such as a neck pillow. The wristband 64 can be attached to a wrist of a user such that the OXT release stimulation device 10" can be arranged at the skin of the user. This allows to provide light of the OXT release stimulation device 10" to the skin of the user.

The OXT release stimulation device 10" includes a lighting unit in form of an LED module 14", a control unit 16''', a massage unit in form of a collapsible membrane 18" and the wristband 64.

The LED module 14" can emit light with different wavelengths and wavelength ranges and as cw or in a pm. In this embodiment the LED module 14" can emit light with a wavelength between 430 nm and 470 nm with a radiant exposure between 0.1 J/cm$^2$ and 100 J/cm$^2$, with a wavelength between 490 nm and 520 nm with a radiant exposure between 0.1 J/cm$^2$ and 100 J/cm$^2$, with a wavelength between 630 nm and 670 nm with a radiant exposure between 0.1 J/cm$^2$ and 300 J/cm$^2$, with a wavelength between 830 nm and 870 nm with a radiant exposure between 0.1 J/cm$^2$ and 300 J/cm$^2$, or with a combination thereof.

The control unit 16''' comprises a processor 22", a user interface in form of a touch display 24", a memory 26", and a sensor in form of a proximity sensor 28". In other embodiments the sensor can also for example be a temperature sensor or any other sensor that allows to detect whether a wrist is received in the wristband 64. In other embodiments the control unit can also comprise another type of sensor, e.g., for determining a duration of light stimulation that ensures stimulation of release of OXT or for detecting presence or absence of the MER.

The control unit 16''' controls the operation of the OXT release stimulation device 10" and in particular of the LED module 14" and the collapsible membrane 18".

The processor 22" allows processing of control signals. Control signals can be received from the touch display 24" provided by the user, from the memory 26", or from the proximity sensor 28". Control signals can for example include light parameters, massage parameters, sensor data, or can be simple control signals for activating or deactivating the LED module 14" and/or the collapsible membrane 18".

The control unit 16''' controls the LED module 14" such that the light is provided to the skin of the user for a duration that ensures stimulation of a release of OXT. In this embodiment the duration for providing the light to the skin of the user in order to stimulate the release of OXT is at least 30 seconds. The collapsible membrane 18" is arranged at the skin of the user when the user wears the wristband 64. In this embodiment the collapsible membrane 18" surrounds the skin of the wrist, when the wrist is inserted in the wristband 64. The collapsible membrane 18" performs cutaneous tactile stimulation to the skin of the user, i.e., it massages the skin of the user, in order to stimulate release of OXT. The parallel usage of light stimulation and cutaneous tactile stimulation allows an improved stimulation of the release of OXT.

The third embodiment of the OXT release stimulation device 10" can for example be used for long term stimulation of the release of OXT during the third trimester of pregnancy in order to reduce the risk of PPD. The third embodiment of the OXT release stimulation device 10" can furthermore for example be used for facilitating the induction of labor by increasing the OXT level in the user. One or more of the OXT release stimulation devices 10" can be worn by the user.

Figure 6:
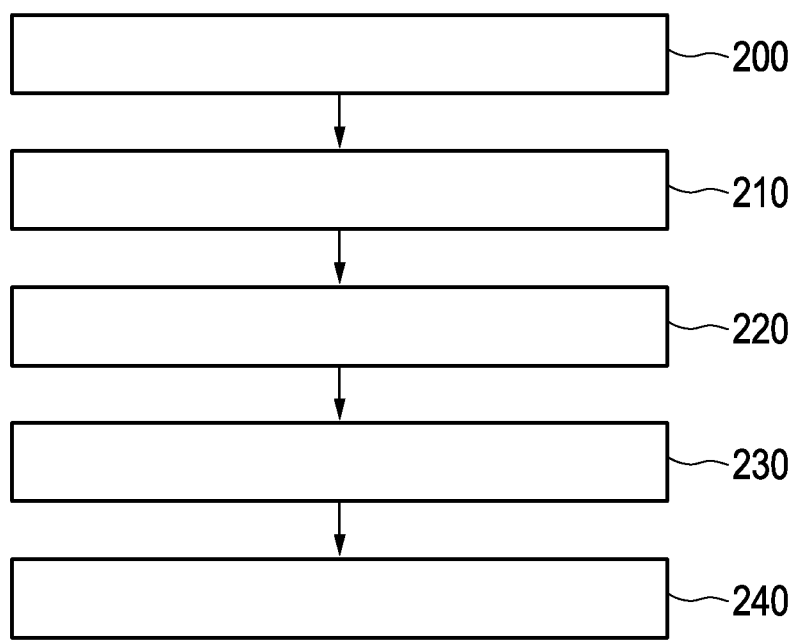
FIG. 6 shows an embodiment of the method for operating the breast pump.

FIG. 6 shows an embodiment of the method for operating a breast pump. The breast pump comprises an OXT release stimulation device, a breast shield, and a pressure source. The OXT release stimulation device comprises a lighting unit for providing light and a control unit for controlling the lighting unit. The breast shield is used for receiving a breast of a user.

In step 200 the breast of the user is received in the breast shield.

In step 210 of the method light is emitted. The light has a wavelength between 430 nm and 470 nm with a radiant exposure between 0.1 J/cm$^2$ to 100 J/cm$^2$, a wavelength between 490 nm and 520 nm with a radiant exposure between 0.1 J/cm$^2$ and 100 J/cm$^2$, a wavelength between 630 nm and 670 nm with a radiant exposure between 0.1 J/cm$^2$ and 300 J/cm$^2$ or a wavelength between 830 nm and 870 nm with a radiant exposure between 0.1 J/cm$^2$ and 300 J/cm$^2$. Alternatively a combination of two or more wavelengths from the light with a wavelength between 430 nm and 470 nm with a radiant exposure between 0.1 J/cm$^2$ to 100 J/cm$^2$, a wavelength between 490 nm and 520 nm with a radiant exposure between 0.1 J/cm$^2$ and 100 J/cm$^2$, a wavelength between 630 nm and 670 nm with a radiant exposure between 0.1 J/cm$^2$ and 300 J/cm$^2$, and a wavelength between 830 nm and 870 nm with a radiant exposure between 0.1 J/cm$^2$ and 300 J/cm$^2$ can be emitted. Light with only one specific wavelength can be provided or a range of wavelengths or ranges of wavelengths. The radiant exposure can be adjusted accordingly for each wavelength or wavelength ranges emitted.

In step 220 it is provided that the emitted light is provided to the skin of the user for a duration that ensures that release of OXT is stimulated. In this embodiment the duration is at least 30 seconds. This allows to stimulate the release of OXT.

In step 230 cycles of alternating increased pressure and reduced pressure are generated in the breast shield to extract milk from the breast of the user. The pressure source is used for generating the cycles of alternating increased and reduced pressure in the breast shield. In this embodiment the pressure source is an electronic vacuum pump. In other embodiments the vacuum pump can be a manually operated vacuum pump, such as a vacuum pump operated with a handle.

In step 240 massaging of the skin of the user is performed. In this embodiment the OXT release stimulation device includes a massaging unit that performs the massaging of the skin of the breast of the user. In other embodiments the massaging can be performed manually.

Steps 230 and 240 are optional and can be performed in opposite order.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit, processor, or device may fulfill the functions of several items recited in the claims. The mere fact that certain measures are recited in mutually different dependent claims does not indicate that a combination of these measures cannot be used to advantage.

Operations like emitting light, providing that the emitted light is provided to the skin of the user for a duration that ensures stimulation of the release of OXT, providing light to the skin of the user, generating cycles of alternating increased and reduced pressure in the breast shield, or massaging of the skin of the user, et cetera performed by one or several units or devices can be performed by any other number of units or devices. These operations and/or the method can be implemented as program code means of a computer program and/or as dedicated hardware.

A computer program may be stored/distributed on a suitable medium, such as an optical storage medium, or a solid-state medium, supplied together with or as part of other hardware, but may also be distributed in other forms, such as via the Internet, Ethernet, or other wired or wireless telecommunication systems.

Any reference signs in the claims should not be construed as limiting the scope.

The present invention relates to an OXT release stimulation device that can be arranged at or close to skin of a user. The OXT release stimulation device comprises a lighting unit and a control unit. The control unit controls the lighting unit such that the lighting unit provides light with specific wavelengths and radiant exposures to the skin of the user for a duration that ensures stimulation of a release of OXT. Release of OXT allows to stimulate a MER and thus to support milk extraction, e.g. when the OXT release stimulation device is used with a breast pump. The OXT release stimulation device can furthermore allow to reach an OXT level during pregnancy that allows to reduce the risk of PPD or that allows to facilitate induction of labor.

The invention claimed is:

1. An oxytocin release stimulation device configured to be arranged at or close to skin of a user and which comprises:
    a lighting unit for emitting light with a wavelength between 430 nm and 470 nm with a radiant exposure between 0.1 J/cm$^2$ and 100 J/cm$^2$, with a wavelength between 490 nm and 520 nm with a radiant exposure between 0.1 J/cm$^2$ and 100 J/cm$^2$, with a wavelength between 630 nm and 670 nm with a radiant exposure between 0.1 J/cm$^2$ and 300 J/cm$^2$, with a wavelength between 830 nm and 870 nm with a radiant exposure between 0.1 J/cm$^2$ and 300 J/cm$^2$, or with a combination thereof, and
    a control unit configured for controlling the lighting unit such that the light is provided to the skin of the user for a duration that ensures stimulation of a release of oxytocin.

2. The oxytocin release stimulation device according to claim 1, wherein the duration for providing the light to the skin of the user in order to stimulate a release of oxytocin is at least 30 seconds.

3. The oxytocin release stimulation device according to claim 2, wherein the lighting unit is configured for emitting the light as continuous wave or in a pulsed mode.

4. The oxytocin release stimulation device according to claim 3, comprising an attachment unit configured for attaching the lighting unit at or close to the skin of the user in order to provide the light to the skin of the user.

5. The oxytocin release stimulation device according to claim 3, configured to provide the light to the skin of a breast of the user.

6. The oxytocin release stimulation device according to claim 3, comprising a massage unit configured to be arranged at the skin of the user and to perform cutaneous tactile stimulation to the skin of the user in order to stimulate release of oxytocin.

7. The oxytocin release stimulation device according to claim 3, configured for providing the light to the skin of the user as a combination of a wavelength between 430 nm and 470 nm with a radiant exposure between 0.1 J/cm$^2$ and 100 J/cm$^2$, a wavelength between 490 nm and 520 nm with a radiant exposure between 0.1 J/cm$^2$ and 100 J/cm$^2$, a wavelength between 630 nm and 670 nm with a radiant exposure between 0.1 J/cm$^2$ and 300 J/cm$^2$, and a wavelength between 830 nm and 870 nm with a radiant exposure between 0.1 J/cm$^2$ and 300 J/cm$^2$ in order to stimulate milk ejection reflex and/or for providing the light to the skin of the user with alternating wavelengths once milk ejection reflex has been triggered.

8. The oxytocin release stimulation device according to claim 3, wherein the lighting unit comprises a light source for generating the light and a light delivery unit for providing the light to the skin of the user, and wherein at least the light delivery unit is configured to be arranged at or close to the skin of the user in order to provide light to the skin of the user.

9. A breast pump for extracting milk comprising:
    an oxytocin release stimulation device according to claim 1,
    a breast shield for receiving a breast of the user therein, and
    a pressure source in air-ducting connection to the breast shield for generating cycles of alternating increased pressure and reduced pressure in the breast shield to extract milk from the breast of the user.

10. The breast pump according to claim 9, wherein the breast pump comprises a breast unit and a base unit, wherein the breast unit comprises the breast shield and wherein the breast unit is configured to be arranged at the breast of the user, wherein the base unit comprises the pressure source and a power supply for providing power, and wherein the breast unit and the base unit are connected via a connection line comprising an air-duct and a power line.

11. A method for operating the breast pump according to claim 9 comprising the steps of:
receiving the breast of the user in the breast shield,
emitting the light with a wavelength between 430 nm and 470 nm with a radiant exposure between 0.1 J/cm$^2$ and 100 J/cm$^2$, with a wavelength between 490 nm and 520 nm with a radiant exposure between 0.1 J/cm$^2$ and 100 J/cm$^2$, with a wavelength between 630 nm and 670 nm with a radiant exposure between 0.1 J/cm$^2$ and 300 J/cm$^2$, with a wavelength between 830 nm and 870 nm with a radiant exposure between 0.1 J/cm$^2$ and 300 J/cm$^2$, or the combination thereof, and
providing that the emitted light is provided to the skin of the user for a duration that ensures stimulation of the release of oxytocin.

12. The method according to claim 11 further comprising the step of generating cycles of alternating increased pressure and reduced pressure in the breast shield to extract milk from the breast of the user.

13. A use of light with a wavelength between 430 nm and 470 nm with a radiant exposure between 0.1 J/cm$^2$ and 100 J/cm$^2$ light with a wavelength between 490 nm and 520 nm with a radiant exposure between 0.1 J/cm$^2$ and 100 J/cm$^2$ light with a wavelength between 630 nm and 670 nm with a radiant exposure between 0.1 J/cm$^2$ and 300 J/cm$^2$ light with a wavelength between 830 nm and 870 nm with a radiant exposure between 0.1 J/cm$^2$ and 300 J/cm$^2$ or a combination thereof provided to skin of a user for stimulating a release of oxytocin.

* * * * *